(12) United States Patent
Penterman et al.

(10) Patent No.: US 9,663,813 B2
(45) Date of Patent: May 30, 2017

(54) METHOD FOR FILTERING A BIOLOGICAL SAMPLE

(71) Applicant: Biocartis NV, Mechelen (BE)

(72) Inventors: Roel Penterman, Tisselt (BE); Bart Van Meerbergen, Sint-Job-in-'t-Goor (BE)

(73) Assignee: Biocartis NV, Mechelen (BE)

( * ) Notice: Subject to any disclaimer, the term of this patent is extended or adjusted under 35 U.S.C. 154(b) by 55 days.

(21) Appl. No.: 14/405,539

(22) PCT Filed: Jun. 26, 2013

(86) PCT No.: PCT/EP2013/063333
§ 371 (c)(1),
(2) Date: Dec. 4, 2014

(87) PCT Pub. No.: WO2014/009151
PCT Pub. Date: Jan. 16, 2014

(65) Prior Publication Data
US 2015/0132793 A1    May 14, 2015

(30) Foreign Application Priority Data

Jul. 9, 2012 (EP) .................................. 12175581

(51) Int. Cl.
*C12Q 1/24*     (2006.01)
*C12N 1/06*     (2006.01)
*C12M 1/00*     (2006.01)
*C12N 1/00*     (2006.01)

(52) U.S. Cl.
CPC .............. *C12Q 1/24* (2013.01); *C12M 47/06* (2013.01); *C12N 1/005* (2013.01); *C12N 1/06* (2013.01)

(58) Field of Classification Search
None
See application file for complete search history.

(56) References Cited

U.S. PATENT DOCUMENTS

| 5,314,624 A * | 5/1994 | Kawakura ........... A61M 1/3472 |
| | | 210/645 |
| 2010/0255474 A1* | 10/2010 | Russwurm ............. C12Q 1/689 |
| | | 435/6.13 |

FOREIGN PATENT DOCUMENTS

| BE | WO 2012168003 A1 * | 12/2012 | ............... C12Q 1/04 |
| WO | WO 2008/017097 | 2/2008 | ............... C12Q 1/00 |
| WO | WO 2009/015484 | 2/2009 | ............... C12N 1/00 |
| WO | WO 2011/070507 | 6/2011 | ............... C12Q 1/68 |

OTHER PUBLICATIONS

International Search Report for International Application No. PCT/EP2013/063333, Oct. 15, 2013.
European Search Report for European Patent Application No. 12 17 5581, Oct. 15, 2012.

* cited by examiner

*Primary Examiner* — Renee Claytor
*Assistant Examiner* — Michelle F Paguio Frising
(74) *Attorney, Agent, or Firm* — Kusner & Jaffe

(57) ABSTRACT

A method for filtering a sample comprising the steps of: (a) providing a sample with eukaryotic cells and containing or suspected to contain a micro-organism; (b) performing a selective lysis of the eukaryotic cells to obtain a lysed sample; (c) filtering the lysed sample obtained in step (b) through a filter arranged to retain the micro-organism; and (d) washing the filter with a detergent based wash buffer to selectively solubilize proteins originating from the eukaryotic cells retained by the filter, by passing the detergent based wash buffer through the filter, to remove protein clogs from the filter in order to allow an additional step (c) of filtering said lysed sample.

21 Claims, 3 Drawing Sheets

METHOD FOR FILTERING A BIOLOGICAL SAMPLE

FIELD OF INVENTION

The present invention relates in a general manner to the detection of low concentrations of micro-organisms in a sample containing a large number of other cells, and more particularly relates to a method of filtration of a blood sample after selective lysis of blood cells to selectively retain pathogens onto a filter while removing blood cellular material such as DNA and proteins.

BACKGROUND OF THE INVENTION

Molecular diagnostics aims at the rapid detection of minute amounts of pathogens (typically bacteria) in samples such as blood. However, blood is a complex matrix and comprises white blood cells (leukocytes) for the adaptive immune system, red blood cells (erythrocytes) for oxygen transport, and platelets (thrombocytes) for wound healing. This composition complicates the direct detection of pathogens in samples such as whole blood, which contain a high amount of cellular material such as DNA and proteins.

Therefore, methods for enriching pathogens while removing blood cellular material from a blood sample are required.

In a known method, pathogens are collected onto a filter by filtration of large volume blood samples after a selective lysis of blood cells.

In the filtration step, inhibitory components such as DNA or proteins are removed while the pathogens are retained onto the filter.

The International patent application WO-A-2011/070507 discloses a method for selective lysis of eukaryotic cells within a sample containing or suspected to contain micro-organisms, wherein a detergent and a buffer are added to said sample to obtain a solution which is further incubated for a time period sufficiently long enough to lyse the eukaryotic cells. This method permits processing of blood samples having a volume of the order of 5 to 10 ml by lysing the white and red blood cells in the sample, degrading the white blood cell DNA while a substantial part (i.e. more than 20%, 40%, 60%, 80%, 90% or even more than 95%) of the micro-organisms remains alive, or if killed by the treatment, still comprise the bacterial DNA within the cell wall. Said micro-organisms can subsequently be enriched by a filtration step so that inhibitory components such as DNA or proteins are removed while the pathogens are retained onto the filter with their bacterial DNA within the cell wall.

It is important that all the available volume of sample is filtered to collect a maximum of micro-organisms onto the filter. However, when the method is applied, the filter usually gets clogged before the sample is completely filtered, due, for example, to the presence of proteins in the sample that are also retained by the filter. This clogging leads to an abortion of the filtration thus stopping the whole processing. Therefore, the existing method does limit the quantity of sample that can be processed on a filter.

SUMMARY OF THE INVENTION

The present invention aims to solve these aforementioned drawbacks and first proposes a method for filtering a sample with eukaryotic cells without the risk of limiting the volume of sample that can be filtered, so that the sensitivity of the method is increased in comparison to existing methods. Such a filtering method may be used in a general method of detecting micro-organisms in complex samples containing a high background of proteins and/or nucleic acids.

With this goal in mind, a first aspect of the invention is a method for filtering a sample comprising the steps of:
(a) providing a sample with eukaryotic cells and containing or suspected to contain a micro-organism;
(b) performing a selective lysis of the eukaryotic cells to obtain a lysed sample;
(c) filtering the lysed sample obtained in step (b) through a filter arranged to retain the micro-organism;
(d) washing the filter with a detergent based wash buffer to selectively solubilize substances other than the micro-organism retained by the filter, by passing the detergent based wash buffer through the filter, to remove clogs consisting of the substances other than the micro-organism from the filter in order to allow an additional step (c) of filtering said lysed sample;
(e) repeat step (c) at least 1 time.

The present invention circumvents the clogging of the filter by substances originating from the sample matrix or eukaryotic cells by the step of washing the filter to remove the clogs from the filter, so that the lysed sample may be entirely filtered, without stops due to a significant decrease of permeability of the filter. The selective removal of the clogs is performed by the wash buffer solution containing a detergent, so that only the substances other than the micro-organism are removed from the filter. The micro-organisms accumulated onto the filter are not removed or degraded by this buffer wash solution, so that they remain on the filter for further processing in order to be detected or analyzed.

Advantageously, the substances other than the micro-organism are proteins originating from the eukaryotic cells. It has been noticed that proteins originating from the eukaryotic cells are easily retained by the filter and clog the latter, so that the method according to the present invention helps to perform a selective removal of these protein clogs from the filter.

Advantageously, the detergent wash buffer is a phosphate buffered saline solution with a pH greater than 5 and lower than 9 and contains a surfactant as the detergent. Selective washing of the substances other than the micro-organisms is achieved.

Advantageously, the surfactant is sodium dodecyl sulfate (SDS) and the detergent wash buffer contains between about 0.2% and about 0.5% sodium dodecyl sulfate (SDS) in volume. Preferably the surfactant is sodium dodecyl sulfate (SDS) and the detergent wash buffer contains 0.3% sodium dodecyl sulfate (SDS) in volume. This particular concentration of sodium dodecyl sulfate achieves the selective dissolution of only the substances other than the micro-organisms such as proteins originating from the eukaryotic cells. Ideally, the concentration of SDS is from 0.2% to 0.5%, preferably from 0.25% to 0.35%, more preferably from 0.27% to 0.33% in volume. The detergent is SDS since this detergent is known to have a pronounced effect on proteins. It will interact with the proteins in such way that it denatures the proteins, reduces sulfide bonds and will result in a final net negative charge depending on the mass of the protein. Key is the concentration of the detergent: it should effectively help opening the filter, yet it may not lead to lysis of the pathogens already collected.

In a preferred embodiment of the present invention, the method comprises a step of detecting clogging of the filter during the step (c) of filtering said lysed sample. The method monitors the clogging of the filter, so that appropriate action can be undertaken in relation with the clogging of the filter.

Ideally, the step (d) of washing the filter is performed when a clogging of the filter is detected e.g. by measuring a pressure build up in the filter chamber. The filtration being jeopardized if the filter is clogged, the washing step is performed when a clogging is detected, so that the process does not comprises any unnecessary washing operation: the washing is performed only if the filter is clogged.

Advantageously, the step (b) of selective lysis of eukaryotic cells comprises:

(b1) a step of adding a lysing detergent and an alkaline buffer to said sample, followed by (b2) a step of incubating the sample for a time period sufficiently long to selectively lyse the eukaryotic cells and degrade the eukaryotic DNA simultaneously. This method ensures a suitable destruction of the physical integrity of the membrane of the eukaryotic cells, without any attempt to degrade the integrity of the micro-organism.

In one embodiment, said sample is mammalian blood sample. The method enhances the filtration if the sample is a blood sample with an effective washing of the lysed blood cells that are retained by the filter.

In one embodiment, the blood sample is whole blood.

The method according to the present invention gives good results when the blood sample originates from a patient suffering from a systemic inflammatory response syndrome (SIRS). Such blood samples originating from patients suffering from SIRS have been successfully filtered with the method according to the present invention, even if the blood coagulation cascade is activated before processing the blood sample.

In one embodiment of the present invention, the filtering step (c) is performed during a first predetermined time and the washing step (d) is performed during a second predetermined time. This embodiment limits the filtering to a first time determined so that the clogging of the filter does not limit the filtration, and limits the washing step to a second time determined so that the washed filter will allow another step of filtration. The filter is regularly washed during the filtration of the lysed sample and the filtering and washing steps are done in a sequential mode before any clogging, so that the filter stays open for a longer time and larger volumes can be processed.

Advantageously, the first predetermined time ranges from 20 to 80 seconds, preferably from 50 to 70 seconds and more preferably from 55 to 65 seconds and the second predetermined time ranges from 5 to 25 seconds, preferably from 5 to 20 seconds and more preferably from 5 to 15 seconds. These time periods allow filtering efficiently blood samples originating from patients such as patients suffering from a systemic inflammatory response syndrome (SIRS) or endocarditis.

In another embodiment of the present invention, the method further comprises a step of lysing said micro-organism and a nucleic acid based molecular assay to detect the micro-organism.

The invention is also related to a device for the filtration of a sample, comprising:
- a lysis chamber for accepting a sample with eukaryotic cells and containing or suspected to contain a micro-organism and for performing a selective lysis of the eukaryotic cells to obtain a lysed sample,
- a filter connected to the lysis chamber for filtering the lysed sample after the selective lysis, said filter being arranged to retain said micro-organism on the filter, and
- a reservoir connected to the filter and containing a detergent based wash buffer to selectively solubilize substances other than the micro-organism retained by the filter, to remove clogs consisting of the substances other than the micro-organism from the filter.

The device according to the present invention provides a way to wash the filter if it is clogged during filtration. Indeed, the detergent based wash buffer is selected to dissolve only the substances other than the micro-organisms such as the proteins originating from the eukaryotic cells, and the reservoir containing the detergent based wash buffer is connected to the filter to allow a washing of the filter. The filtration can be operated even if some proteins clog the filter, without any loss of micro organisms which are not dissolved by the detergent based wash buffer.

In one embodiment, the lysis chamber presents a volume of 40 ml or less.

Advantageously, the detergent wash buffer is a phosphate buffered saline solution with a pH greater than 5 and lower than 9 and contains between about 0.2% and about 0.5% sodium dodecyl sulfate (SDS) in volume, preferably about 0.3%.

Advantageously, the device further comprises a sensor arranged to measure a clogging of the filter. Ideally the sensor is a pressure sensor. As an alternative, the sensor may be an optical sensor which measures a deflection of a pump of the device and is integrated in the device. Advantageously the aforementioned pump can be operated at fixed pressure.

Advantageously, the device further comprises a detection chamber for performing a nucleic acid based molecular assay to detect the micro-organism.

DEFINITIONS

"Blood cells" in the context of the present invention relates to mammalian cells present in blood and includes red blood cells (erythrocytes), white blood cells (leukocytes) and blood platelets (thrombocytes).

"Whole blood" in the context of the present invention relates to unprocessed blood comprising blood plasma and cells, treated with an anti-coagulant.

"Sample" relates to an aqueous suspension comprising cellular material and comprises body fluids such as lymph, cerebrospinal fluid, blood (whole blood and plasma), saliva, but also comprises e.g. the aqueous fraction of homogenized suspensions such as e.g. muscles, brain, liver, or other tissues.

"Eukaryotic" in the present invention relates to any type of eukaryotic organism excluding fungi, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans.

"Selective lysis" as used in the present invention is obtained when in a sample (such as blood) the percentage of micro-organism cells (such as bacterial cells) in that sample that remain intact is significantly higher (e.g. 2, 5, 10, 20, 50, 100, 250, 500, or 1000 time more) compared to the percentage of the eukaryotic cells from the organism from which the blood sample is collected that remain intact. For instance, without being limited to this particular method, a selective lysis of eukaryotic cells may be performed by the method disclosed in the document WO-A-2011/070507.

"Micro-organism" as used in the present invention relates to bacteria (gram positive and gram negative bacteria, as well as bacterial spores) and unicellular fungi such as yeast and molds, which are present in the organism from which a sample has been collected, typically as a pathogen.

BRIEF DESCRIPTION OF THE DRAWINGS

Other characteristics and advantages of the present invention will appear more clearly from the following detailed description of particular non-limitative examples of the invention, illustrated by the appended drawings where:

FIG. 2a with pathogen *P. aeruginosa* and FIG. 2b with pathogen *C. albicans*.

DETAILED DESCRIPTION

Experiment 1

Effect on Filtration

Figure 1:
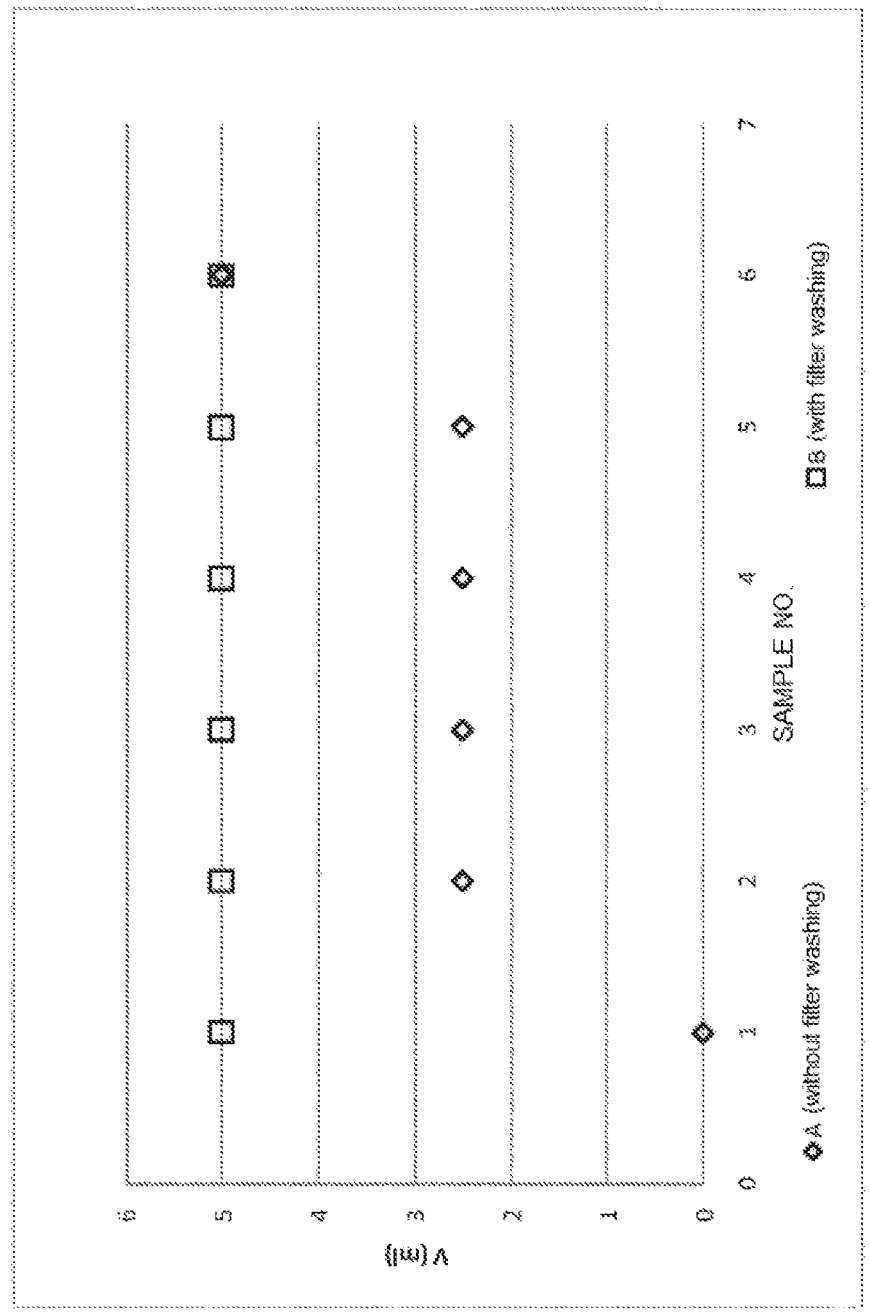
FIG. 1 represents comparative results of filtering blood samples with and without applying the method according to the present invention.

FIG. 1 represents comparative results of filtering 5 ml blood samples originating from patients suffering from a systemic inflammatory response syndrome (SIRS), with (samples A) and without (samples B) the washing step according to the present invention.

The blood samples were all (A & B) subjected to a selective lysis of the eukaryotic cells with the addition of a lysis buffer consisting of a 1M $HCO_3^-/CO_3^{2-}$ buffer (pH 10.0) with 1% sodium dodecyl sulfate (SDS). After mixing with the blood sample, the selective lysis occurred, and was stopped after three minutes using a third buffer that lowers the pH.

All blood samples have been processed through a filter arranged to retain micro organisms. Two series of six blood samples have been filtered:
  six blood samples prepared with a standard method without the filter washing during the filtration after the selective lysis (blood samples A), and
  six blood samples prepared with the method according to the present invention with the filter washing step during the filtration after the selective lysis (blood samples B). For these samples B, the filtration step lasted one minute and the washing step lasted ten second, the steps being done in a sequential mode.

The blood samples were prepared using disposable cartridges arranged with a lysis chamber connected to such filter, the cartridges having an additional reservoir connected to the filter and containing a wash buffer being a phosphate buffered saline solution which contains 0.3% sodium dodecyl sulfate (SDS) in volume, for blood samples B. Blood samples A were directly and only subjected to the filtering operation, and blood samples B were subjected to a filtration step of one minute, interrupted by a ten seconds step of washing the filter with the phosphate buffered saline solution which contains 0.3% sodium dodecyl sulfate (SDS) in volume, followed by a further step of filtering.

The FIG. 1 represents the quantity of liquid filtered for each sample. For the blood samples A, only one blood sample of 5 ml has been fully filtered, only 2-3 ml of four blood samples have been filtered before clogging of the filter, and one blood sample was not filtered at all, the filter being immediately clogged. The six blood samples B have been entirely filtered. This demonstrates that the washing step of the filter enables the filtering of the complete volume of 5 ml of blood samples previously subjected to a selective lysis.

Experiment 2

Comparative Results of Recovery of Pathogens

Figure 2A:
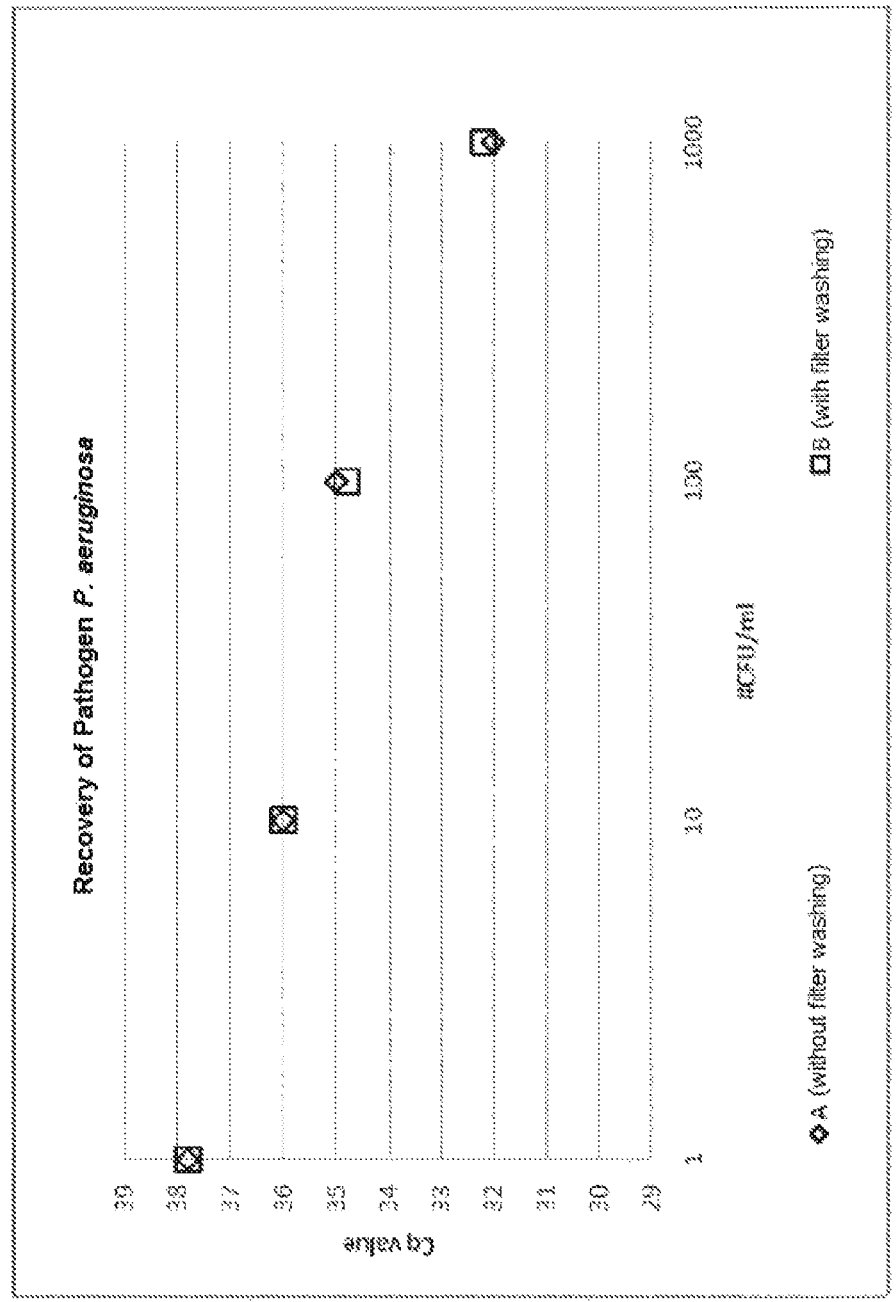
FIGS. 2a and 2b represent comparative results of the detection of different pathogens with and without applying the method according to the present invention.

FIG. 2a represents results of the recovery of a specific pathogen *P. aeruginosa* contained in blood samples of normal healthy donors, using the method according to the present invention, compared to results with a method without washing the filter. Blood samples A represent a baseline with the method without the washing step, and blood samples B were tested with introducing a step of washing during the filtration according to the present invention. The graph shows that there is no effect of the washing of the filter in recovering the pathogen from the blood.

Figure 2B:
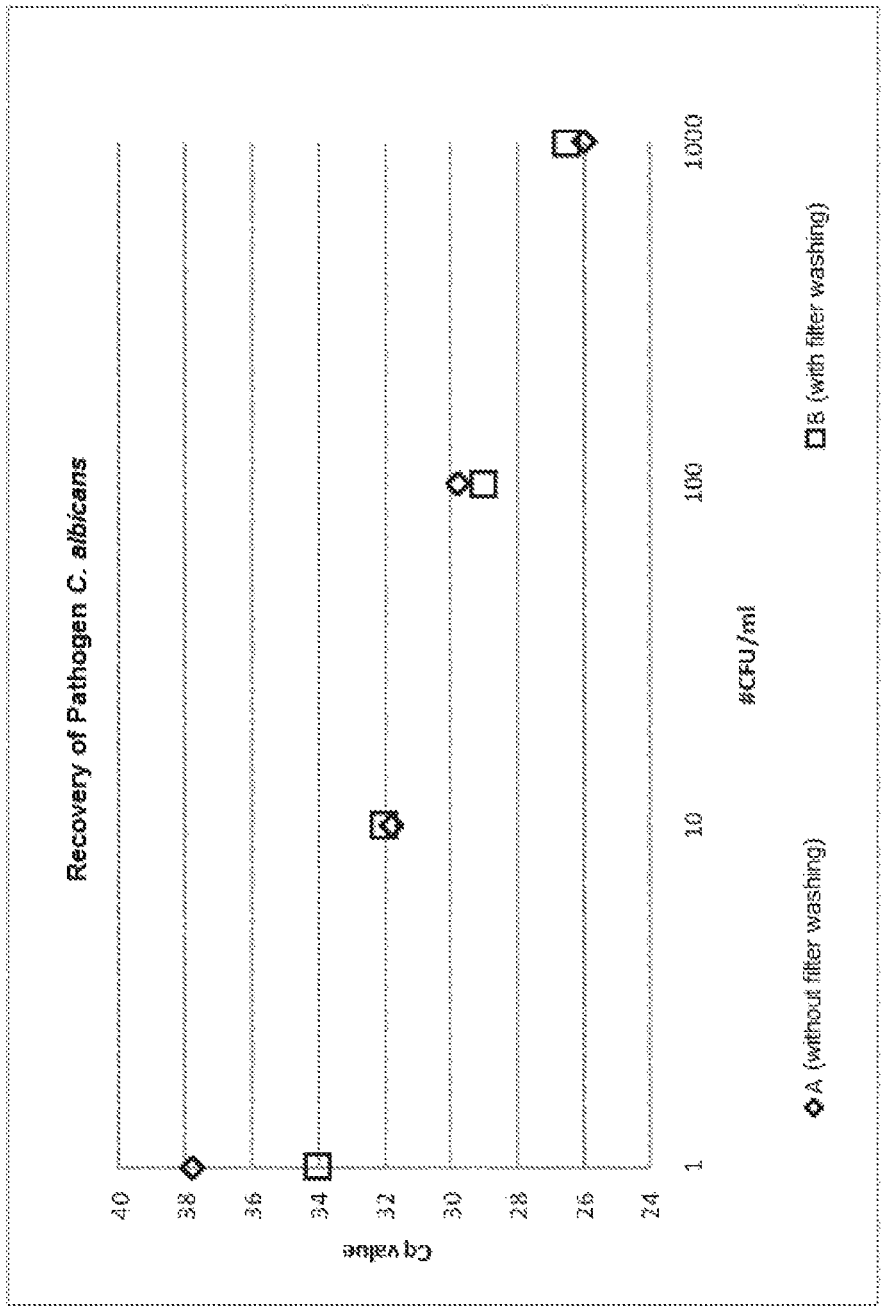

FIG. 2b represents results of the recovery of a specific pathogen *C. albicans* contained in blood samples, using the method according to the present invention, compared to results with a method without washing the filter. This experiment with pathogen *C. albicans* leads also to the conclusion that the method according to the present invention has no deleterious effect on the recovery of the pathogens from the blood, as the blood samples A (baseline, without the washing step of the filter) show similar results to the blood samples B, tested with the washing step during the filtration.

Experiment 3

Effect on Filterable Volume

In a third experiment a disposable cartridge was designed with a filter size which was four times smaller than the standard filter size (1.75 cm2 vs. 7 cm2). Blood samples of 5 ml originating from normal healthy donor blood have been successfully filtered with the method according to the present invention (with a step a washing the filter), which would be similar to 20 ml blood samples filtered through standard sized filters. This is at least two times the filterable volume achievable with the method without the new washing.

It is understood that obvious improvements and/or modifications for one skilled in the art may be implemented, being under the scope of the invention as it is defined by the appended claims. In particular, the selective lysis of the eukaryotic cells may be performed with any known methods using physical, chemical or biological process.

Having described the invention, the following is claimed:
1. A method for filtering a sample to selectively retain micro-organisms onto a filter, the method comprising:
  (a) providing a sample with eukaryotic cells and containing or suspected to contain a micro-organism;
  (b) performing a selective lysis of the eukaryotic cells to obtain a lysed sample;
  (c) filtering a portion of the lysed sample obtained in step (b) through a filter arranged to retain the micro-organism;
  (d) washing the filter with a detergent-based wash buffer having a detergent concentration that selectively solubilizes substances other than the micro-organism retained by the filter, said washing includes passing the detergent-based wash buffer through the filter, to selectively remove clogs consisting of the substances other than the micro-organism from the filter; and (e) repeating step (c) at least one additional time, to filter at least one additional portion of the lysed sample, wherein the detergent concentration in the detergent-based wash buffer is between about 0.2% and about 0.5% by volume.

2. The method according to claim 1, wherein the substances other than the micro-organism are proteins originating from the eukaryotic cells.

3. The method according to claim 1, wherein the detergent-based wash buffer is a phosphate buffered saline solution with a pH greater than 5 and lower than 9 and contains a surfactant as the detergent.

4. The method according to claim 3, wherein the surfactant is sodium dodecyl sulfate (SDS).

5. The method according to claim 4, wherein the detergent-based wash buffer contains about 0.3% SDS in volume.

6. The method according to claim 1, further comprising: detecting clogging of the filter during the step (c) of filtering a portion of said lysed sample.

7. The method according to claim 6, wherein the step (d) of washing the filter is performed when a clogging of the filter is detected.

8. The method according to claim 1, wherein the step (b) of selective lysis of eukaryotic cells comprises:
(b1) a step of adding a lysing detergent and an alkaline buffer to said sample, followed by
(b2) a step of incubating the sample for a time period sufficiently long to selectively lyse the eukaryotic cells.

9. The method according to claim 1, wherein said sample is mammalian blood sample.

10. The method according to claim 9, wherein the blood sample originates from a patient suffering from a systemic inflammatory response syndrome (SIRS) or endocarditis.

11. The method according to claim 1, further comprising a step of lysing said micro-organism.

12. The method according to claim 1, further comprising a nucleic acid-based molecular assay to detect the microorganism.

13. The method according to claim 1, further comprising alternately repeating the step (d) and the step (c) until all of the lysed sample obtained in the step (b) has been filtered.

14. The method according to claim 1, wherein the step (c) of filtering a portion of the lysed sample is performed during a first predetermined time period and the step (d) of washing the filter is performed during a second predetermined time period.

15. The method according to claim 14, wherein the step (c) of filtering a portion of the lysed sample and the step (d) of washing the filter are performed sequentially before any clogging of the filter.

16. The method according to claim 1, wherein the detergent is a surfactant.

17. The method according to claim 16, wherein the surfactant is sodium dodecyl sulfate (SDS).

18. The method according to claim 1, wherein the step (d) of washing the filter is performed when a clogging of the filter is detected.

19. The method according to claim 18, wherein clogging of the filter is detected by sensing pressure.

20. The method according to claim 18, wherein clogging of the filter is detected using an optical sensor.

21. A method for filtering a sample to selectively retain micro-organisms onto a filter, the method comprising:
(a) providing a sample with eukaryotic cells and containing or suspected to contain a micro-organism;
(b) performing a selective lysis of the eukaryotic cells to obtain a lysed sample;
(c) filtering a portion of the lysed sample obtained in step (b) through a filter arranged to retain the micro-organism;
(d) washing the filter with a detergent-based wash buffer having a detergent concentration that selectively solubilizes substances other than the micro-organism retained by the filter, said washing includes passing the detergent-based wash buffer through the filter, to selectively remove clogs consisting of the substances other than the micro-organism from the filter; and
(e) alternately repeating the steps (c) and (d) of filtering the lysed sample and washing the filter, wherein a different portion of the lysed sample obtained in step (b) is filtering during each iteration of step (c),
wherein the detergent concentration in the detergent-based wash buffer is between about 0.2% and about 0.5% by volume.

* * * * *